US006405137B1

(12) United States Patent
Reading

(10) Patent No.: US 6,405,137 B1
(45) Date of Patent: Jun. 11, 2002

(54) METHOD AND APPARATUS FOR PERFORMING CHEMICAL ANALYSIS USING IMAGING BY SCANNING THERMAL MICROSCOPY

(75) Inventor: Michael Reading, London (GB)

(73) Assignee: TA Instruments, Inc., New Castle, DE (US)

(*) Notice: Subject to any disclaimer, the term of this patent is extended or adjusted under 35 U.S.C. 154(b) by 0 days.

(21) Appl. No.: 09/000,521

(22) Filed: Dec. 30, 1997

Related U.S. Application Data

(63) Continuation-in-part of application No. 08/837,547, filed on Apr. 21, 1997, now Pat. No. 6,095,679.
(60) Provisional application No. 60/033,959, filed on Dec. 31, 1996.

(51) Int. Cl.$^7$ ................................................. G01K 5/08
(52) U.S. Cl. ........................... 702/22; 702/24; 702/130; 702/134; 374/137; 374/142; 374/163; 374/164
(58) Field of Search .................. 702/22–24, 27–32, 702/94, 95, 99, 121–123, 130, 133, 134, 136, 150–153, 159, 167, 168, 172, 183, 193, FOR 158, FOR 170, FOR 175, FOR 131, FOR 140, FOR 142, FOR 144, FOR 115–FOR 119; 700/266, 268, 269, 273, 274, 58–60, 66, 85, 186, 187, 192, 193, 195, 259, 264, 299, 300, 302; 382/295, 282; 374/137, 44, 124, 142, 164, 120, 121, 10–13, 163, 130, 132, 141, 5, 31, 43, 57; 356/375, 376, 302, 303, 313, 315, 346, 437–440; 250/306, 234, 440, 11, 307, 309–311, 442.11, 443.1, 338.5, 339.07, 339.08, 339.12, 339.13, 341.1, 341.2, 341.6, 352, 910; 73/105, 1.02, 19.01, 19.02, 23.2, 22, 23, 25, 23.41, 23.35–23.37, 23.42, 25.01, 866.5; 422/50, 55, 62, 67, 68.1, 69, 70, 80, 82.01, 82.02, 82.04, 82.05, 82.09, 82.12, 83, 88–90, 98, 99, 103, 109, 119, 305, 947; 95/82, 83, 87; 96/101–103, 417

(56) References Cited

U.S. PATENT DOCUMENTS

| 5,224,775 A | * | 7/1993 | Reading et al. ................ 374/11 |
| 5,248,199 A | | 9/1993 | Reading ........................ 374/11 |
| 5,281,397 A | * | 1/1994 | Ligon et al. ................ 73/23.37 |
| 5,338,514 A | * | 8/1994 | Morabito et al. .............. 422/89 |
| 5,441,343 A | | 8/1995 | Pylkki et al. ................ 374/137 |
| 5,741,960 A | * | 4/1998 | Payne et al. .................. 422/89 |

FOREIGN PATENT DOCUMENTS

| EP | 0 135 375 A2 | 3/1985 |
| EP | 0 371 572 A2 | 6/1990 |
| WO | WO97/40369 | 10/1997 |

OTHER PUBLICATIONS

Dinwiddie et al., "Thermal Conductivity Contrast Imaging with a Scanning Thermal Microscope", Thermal Conductivity 22, T. W. Tong (ed.) (1994), pp. 668–677 (No month).*
"How Does Tip Tap?" NA Burnham, OP Behrend, F Oulevey, G Gremaud, PJ Gallo, D Gourdon, E Dupas AJ Kulik, HM Pollock and GAD Briggs, accepted for publication in Nanotechnology (Dec. 1996). pp. 67–75.
"Characterizing Polymer Surfaces—Nanoindentation, Surface Force Data, Calorimetric Microscopy" NS Lawson, RH Ion, HM Pollock, DJ Hourston, and M Reading, Physica Scripta T55, 199 (1994). (No month). pp. 201–205.
"Nanoindentation", HM Pollock in : Friction Lubrication, and Wear Technology, (Metals Handbook vol. 18 pp. 419–429), PJ Blau (ed.) American Society for Metals (10th edition, 1992). (No month).

(List continued on next page.)

Primary Examiner—Hal Wachsman
(74) Attorney, Agent, or Firm—Shaw Pittman LLP

(57) ABSTRACT

Sub-micron chemical analysis of the surface and sub-surface of a sample material is performed at, above or under atmospheric pressure, or on for a sample material submerged in a substance. A thermal and/or topographic image of the surface of the sample material is obtained. A location for study is selected using the image. The activation device is positioned over the selected location and surface and/or sub-surface products are ablated, desorbed or decomposed from the sample material to a chemical analyzer for analysis.

38 Claims, 2 Drawing Sheets

OTHER PUBLICATIONS

"Intrepretation of Force Curves in Force Microscopy" NA Burnham, RJ Colton, and HM Pollock, Nanotechnology 4 64–80 (1993). (No month).

"Comparison of Volatiles Constituents and Waxes in Genetically Engineered Tomato", RM Smith, JA Marshall, MR Davey, KC Lowe, and JB Power, Phytochemistry, 1996, 43, 753–758. (No month).

"Pyrolysis– Gas Chromatography Proline, Hydroxyproline and Related Peptides" RM Snuith, SA K Shawkat and WP Hayes, Analyst 1980, 105, 1176–1181. (Dec. 1980).

"Modulated Differential Scanning Calorimetry: I. A. Study of the Glass Transition Behavior of Blends of Poly(metyl methacrylate) and poly(styrene–co–acrylonitrile)", M SOng, A Hammiche, HM Pollock, DJ Hourston, and M Reading, Polymer, 36, 3314–6 (1995). (No month).

"Modulated Differential Scanning Calorimetry: II Studies of Physical Ageing in Polystrene" M Song, DJ Hourston, and HM Pollock, Polymer, 37–243–7. (1996). (No month).

"Deformation in Glassy Polymers" M Song, DJ Hourston, and HM Pollock, J Applied Polymer Science 59, 173–8 (1996). (No month).

"Modulated Differential Scanning Calorimetry: IV Miscibility and Glass Transition Behavior in Poly9methyl methacrylate) and poly(epichlorohydrin) Blends" M Song, A. Hammiche, HM Pollock, M Reading, accepted for publication in Polymer pp. 5661–5665.

"Modulated Differential Scanning Calorimetry VI. Thermal Characterization of Multicomponent Polymers and Interfaces", DJ Hourston, M Song. A Hammiche, HM Pollock, and M Reading, accepted for publication in Polymer (1996). pp. 1,3–7. (No month).

"Modulted Differential Scanning Calorimetry: XI. A Characterization Method for IPN Materials", M Song, DJ Hourston, A Hammiche, HM Pollock, and M Reading, submitted to Thermochimica Acta (1996), pp. 335–338,340–346. (No month).

"Modulated Differential Scanning Calorimetry: VII. Interfacial Macromolecular Diffusion in a Core Shell Latex Particle", M Song, DJ Hourston, A Hammiche, HM Pollock and M Reading, accepted for publication in Thermochimica Acta (1996), pp. 23,24,26–28,30,31. (No month).

"Sub–Surface Imaging By Scanning Thermal Microscopy" A Hammiche, HM Pollock, M Song, and DJ Hourston, Measurement, Science and Technology 7, 142–150 (Feb. 1996).

"Scanning Thermal Microscopy: Sub–Surface Imaging, Thermal Mapping of Polymer Blends, Localized Calorimetry", A Hammiche, HM Pollock, DJ Hourston, M Reading, and M Song, J Vac Sci Technol [/bf B]: Microelectronics and Nanostructures, 14(Mar./Apr. 1996) 1486–1491.

"Localized Thermal Analysis Using a Minaturized Resistive Probe" A Hammiche, M Reading, HM Pollock, M Song, and DJ Hourston, Rev.Sci. Instrum. 67 (12) to be published (Dec. 1996), pp. 4268–4274.

"Sub–Surface SthM Imaging of Blends, With Localized Calorimetric Analysis" A. Hammiche, M. Song, HM Pollock, M Reading, and DJ Hourston, Polymer Preprints (American Chemical Society's Division of Polymer Chemistry), 1996, preprint No. 278, p. 586 only.

"Interfaces in Polymer Blends: SThM Imaging, M–T DSC fingerprinting" HM Pollock, A Hammiche, M Song, DJ Hourston, and M Reading, Polymer Preprints (American Chemical Society's Division of Polymer Chemistry) 1996, preprint No. 246, pp. 69,70. (No month).

"Nanofabrication of Sensors on Cantilever Probe Tips for Scanning Multiprobe", K. Lue, Z. Shi, J. Lai, and A. Majunder, Appl., Phys. Lett. 63(3), Jan. 15, 1996, pp. 325,326.

Mamin, HJ, "Thermal Writing Using A Heated Atomic Force Microscope Tip" Applied Physics Letters, Jul. 15, 1996, pp. 433–435.

IBM Technical Disclosure Bulletin, "Laser Desorption Transfer Sampling", vol. 36, No. 5, May 1, 1993, pp. 87–88.

* cited by examiner

US 6,405,137 B1

METHOD AND APPARATUS FOR PERFORMING CHEMICAL ANALYSIS USING IMAGING BY SCANNING THERMAL MICROSCOPY

The present application is a continuation-in-part of U.S patent application Ser. No. 08/837,547 (now U.S. Pat. No. 6,095,679), filed Apr. 21, 1997, which is hereby incorporated by reference herein in its entirety. The present application also claims the benefit of U.S. Provisional Application No. 60/033,959 (the "Provisional Application"), filed Dec. 31, 1996, which is hereby incorporated by reference herein in its entirety.

BACKGROUND

1. Field of the Invention

The present invention relates to analyzing the chemical nature of materials. More particularly, the present invention relates to sub-micron analysis of chemical properties of a sample material at a particular location of interest by decomposing, desorbing or ablating a small portion of the sample material and transferring the small portion to a chemical analyzer.

2. Background of the Invention

A conventional method for imaging the chemical nature of polymeric systems is imaging Secondary Ion Mass Spectroscopy (SIMS). In imaging SIMS, the surface of a sample is bombarded by a beam of ions (usually argon) that is rastered over the surface. The ions cause material on the surface of the sample to be ejected and ionized. These secondary ions are swept into a mass spectrometer for analysis. SIMS is a very expensive technique that is not easily applicable to insulating samples such as polymers. This is because a charge that builds on the surface of insulating polymer samples deflects the incident ion beam. Although this can be overcome in some cases by bathing the insulating polymer sample with electrons, a great deal of expertise is required to obtain satisfactory results. A further limitation of SIMS is that the sample must be analyzed under high vacuum. It would be desirable in many cases to analyze samples at or above atmospheric pressure or submerged in a substance, for example water.

Another problem with SIMS is that is a continuously destructive imaging technique. As described above, the bombardment of the material by the ion beam causes the surface material to be ejected, thereby destroying the surface material. It would be advantageous to have an imaging system which can image the topology and thermal properties of the material without destroying the surface. It is also desirable to be able to study the material after any damage is done as a result of desorption or pyrolysis. Neither kind of study can be performed using conventional SIMS techniques.

SUMMARY OF THE INVENTION

The present invention allows chemical studies to be performed on the surface and sub-surface of a material. An image of a sample material is created using any conventional sample imaging technique. Using the image, an area of the sample on which to perform analysis is determined. An activation device is positioned at the selected area of interest. The activation device is activated to cause a portion of the sample to be emitted. The emitted portion of the sample is collected and analyzed to determine its chemical properties. The present invention can be used below, at or above atmospheric pressure or submerged in a substance, for example, water.

In a preferred embodiment of the present invention, the activation device is a highly miniaturized resistive probe as described below. In the preferred embodiment, an image of the sample is created using the probe. Using the resulting image, the probe is positioned at a desired location on the surface. Using a selected heating mode, the probe is heated to cause a portion of the sample to decompose or desorb into a gaseous form. The evolved gas is swept into a heated capillary tube, which is positioned close to the probe. The heated capillary tube is connected to a chemical analyzer, which analyzes the evolved gases. The area from which the material was decomposed or desorbed can further be rescanned to assess the volume ablated. The process is then repeated for another selected area.

The process can be placed under computer control. Using a computer the selected area can be scanned. Further, either an operator or the computer can select areas for analysis.

OBJECTS OF THE INVENTION

A first object of the present invention is to provide sub-micron imaging and chemical analysis over a wide-variety of atmospheric pressures, including at or above atmospheric pressure, under a vacuum, and submerged under a substance, for example, water.

Another object of the present invention is to image a sample topology and thermal properties in a non-destructive manner, in addition to obtaining information using pyrolysis and desorption.

Another object of the present invention is to reduce the problems associated with imaging insulators such as polymers.

Another object of the present invention is to provide precise temperature control to increase the resolution of chemical species analysis.

Another object of the present invention is to reduce the cost of conventional sub-micron imaging.

These and other objects of the present invention are described in greater detail in the detailed description of the invention, the appended drawings and the attached claims.

DETAILED DESCRIPTION OF THE INVENTION

Figure 1:
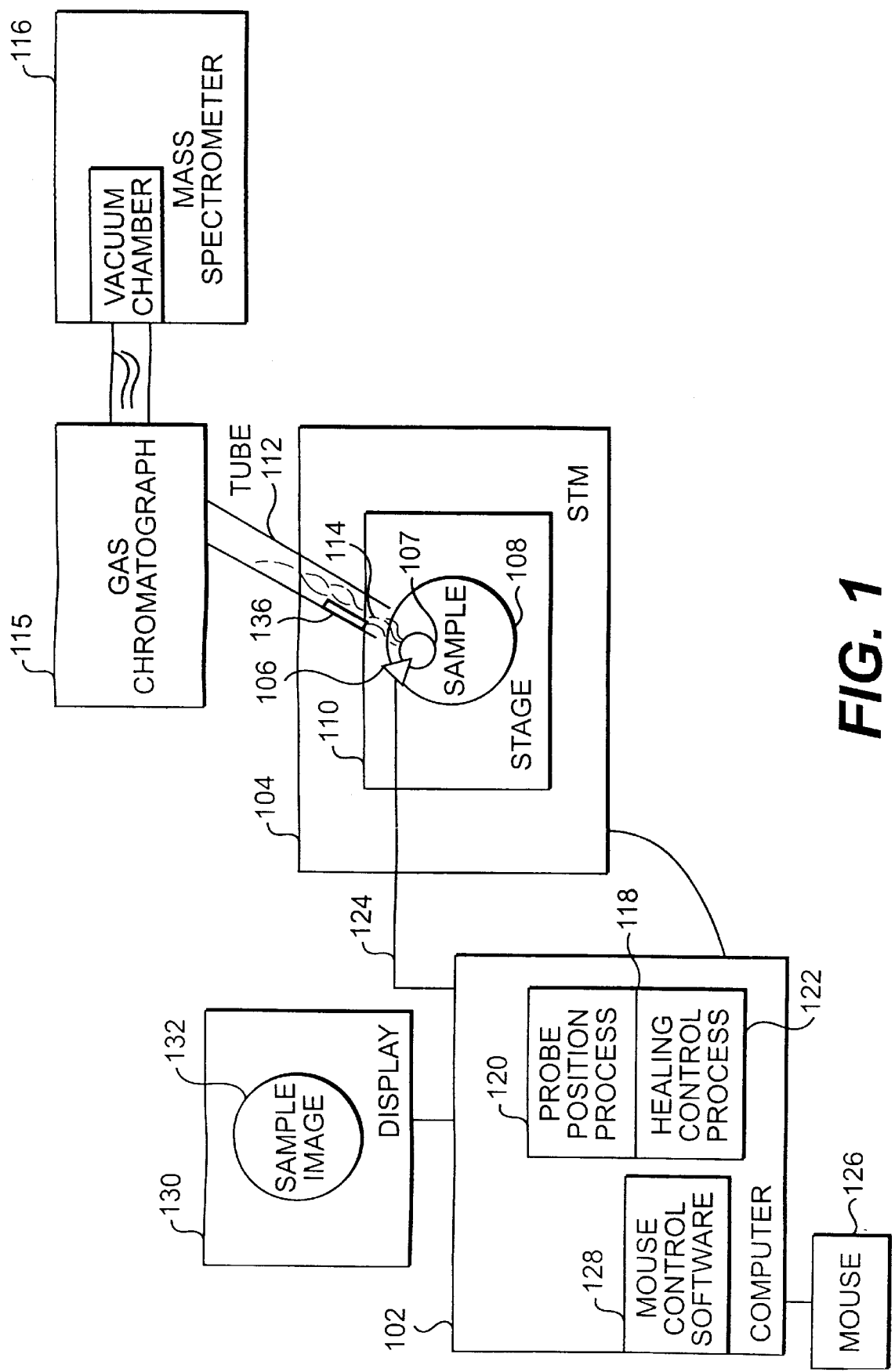
FIG. 1 is a schematic diagram of a sub-micron chemical analysis system according to a preferred embodiment of the present invention.

A preferred embodiment of the present invention is illustrated schematically in FIG. 1. In the preferred embodiment, a computer 102 is operatively coupled to a scanning thermal microscope (STM) system 104. STM 104 includes a probe 106, which is used to analyze local thermal properties at a location 107 of a sample 108, placed on a stage 110 of STM 104. According to the preferred embodiment, a heated capillary tube 112 is placed in close proximity to location 107 to collect evolved gases 114 that result from heating location 107 according to the present invention. In the preferred embodiment, evolved gases 114 are analyzed for their chemical composition by a gas chromatograph 115 and/or a mass spectrometer 116.

STM 104 is preferably the Explorer scanning probe microscope (SPM) manufactured by the Topometrix Corporation, located in Santa Clara, Calif. Probe 106 is preferably a thermal resistive element that functions as both a heater and a sensor. Alternately, probe 106 is heated by a laser and the temperature sensed by a thermocouple. When operating as a heater a current proportional to the desired temperature is passed through probe 106. When operating as a sensor, the resistance of probe 106 varies in response to changes in temperature. A more detailed description of STM 104 and probe 106 is presented in the U.S. Pat. No. 6,095,679, which has been incorporated by reference herein in its entirety.

Probe 106 can be used as a highly localized heat source as well as a detector. When heated by the passage of an electric current through the resistive portion of probe 106, its contact with the sample acts as a point-like heat source. Therefore, no other means of sample heating, such as a laser, is required. The probe 106 is attached to a scanning mechanism, and is controlled to obtain thermal image contrast that corresponds to variations in either thermal conductivity (using DC imaging) or thermal diffusivity (using AC imaging). Examples of such DC or AC imaging are explained in the U.S. Pat. No. 6,095,679.

In the preferred embodiment, computer 102 controls the position and the temperature of probe 106 by executing a probe control process 118. Thus, the scanning mechanism in the preferred embodiment is computer 102. Computer 102 executes a probe position process 120. Probe position process 120 sends commands to STM 104 to control the position of probe 106. This position control can simply be a command to probe 106 to move to a particular location, for example location 107. In addition, the position control can be complex so as to effectuate a scan or raster of a particular area of interest. Programming computer 102 to perform the functions described herein for probe position process 120 is well-known to those skilled in the art.

Computer 102 also executes a heating program process 122, which sends probe control commands to probe 106 to cause it to heat according to a selected or calculated temperature program. The temperature program can be selected or chosen in a number of well-known ways. For example, the temperature program can be selected by choosing the exact parameters that describe the temperature program. Alternately, the temperature program can be entered by parameters that are then used to calculate the desired temperature program. Programming computer 102 to perform the functions described herein performed by heating control process 122 is well-known to those skilled in the art.

Several methods for causing probe 106 to generate the desired temperature program can be used with the present invention. In the preferred embodiment, computer 102 sends probe control commands to STM 104 in a well-known manner over an interface 124. STM 104 receives the probe control commands and causes a current to flow through probe 106 to generate the requested temperature program.

According to the preferred embodiment of the present invention, a particular location, for example location 107, on sample 108 at which to perform a localized thermal analysis is selected by first obtaining a thermal and/or topographic image of the sample. The thermal and/or topographic image can be obtained by any of the techniques disclosed in the U.S. Pat. No. 6,095,679, or any other technique. Using the thermal and/or topographic image, the particular location is selected.

In the preferred embodiment, selection is performed using a pointing device 126. For example, pointing device 126 can be a conventional mouse device controlled by mouse control software 128 executing on computer 102. Preferably, the thermal and/or topographic image is generated on a display device 130. Referring to FIG. 1, a thermal image 132 of sample 108 is illustrated on display device 130. Display device 130 can be any of a number of well-known cathode ray tube (CRT) devices that can be coupled to computer 102. Once the area is selected, probe position process 120, executing on computer 102, converts the selected location to probe position control commands. Probe position process 120 sends the probe position control commands to STM 104 to cause probe 106 to be positioned at location 107. Probe 106 is preferably placed approximately a micron above the surface of sample 108 at location 107.

Once probe 106 is located at the position 107, probe position process 120 places probe 106 on the surface of sample 108. Preferably, this is accomplished by placing the probe in contact with the surface of sample 108 at location 107 and applying a known force to probe 106 to maintain contact with the surface of sample 108. Sample 108 is then heated by heating probe 106. Preferably, sample 108 is heated by applying one of the heating modes described below to probe 106. Alternately, probe 106 can be placed at a known distance above the surface of sample 108. Sample 108 would then be heated, preferably by applying one of the heating modes described below to probe 106.

When probe 106 is properly positioned at location 107, a heating mode is selected to cause probe 106 to heat sample 108 at location 107. The heating modes are selectable or can be pre-selected, as by choosing one mode to be a default mode. There are several heating modes available in the preferred embodiment:

a) Temperature Ramp Mode: Probe 106 is placed on the area of interest and its temperature ramped. Adsorbed material is driven off at low temperatures. Then decomposition products are generated at higher temperatures.

b) Heat Pulse mode: Probe 106 is heated to some temperature above the normal decomposition or desorption temperature for sample 108. Probe 106 is then briefly placed on the surface of sample 108. Desorption and decomposition products are generated. The amount of time that probe 106 remains in contact with the surface of sample 108 can be used to regulate the size of the region over which decomposition/desorption occurs. The heat pulse mode is alternately referred to as a tapping mode. That is the hot probe 106 is tapped on the surface of sample 108 to heat it.

c) Transfer Mode: Probe 106 is cleaned by heating to a high temperature. Then probe 106 is allowed to cool. Probe 106 is then placed on the surface of sample 108 and raised. Material from the surface of sample 108 is adsorbed onto the probe. The adsorbed material can then be desorbed by flash heating. The process can be repeated as required to obtain sufficient material for analysis. Because repetition may be required, this process is preferably automated. That is computer 102 controls the process of cleaning, cooling, lowering, raising and flash heating of probe 106.

An alternative technique for using the transfer mode is to coat the tip of probe 106 with a material that assists the adhesion of the surface material to probe 106. For example, probe 106 can be dipped in the requisite fluid. Any adhesion promoting or reactive fluid can be used. A reactive fluid chemically reacts with the surface of sample 108 to promote adhesion products. To assist drying, probe 106 is preferably warmed. Probe 106 is then placed on the surface of sample 108. Surface material can adhere to the coating. Alternately, probe 106 can be warmed to assist the adhesion process. Probe 106 can then be cooled and raised. Then the adhesion products can be desorbed through flash heating. During chemical analysis, the decomposition products of the coating would be known, and therefore can be eliminated from the analysis. Alternately, the raised probe 106 can be moved to a different location where it is dipped into a transfer medium. The transfer medium dissolves the sample into a small dot of the new material. This product is then analyzed by any analytical technique, including conventional high performance liquid chromograph (HPLC) and electrophoresis. Using a coating that is not water-soluble, the transfer mode can be applied to a sample that is under water. Materials submerged in substance other than water can be studied by using a solvent-insoluble coating, or any coating not soluble by the substance in which the material is submerged. The particular coating that is used in the transfer mode can contain reactive species to obtain specific products.

d) Ballistic Mode: Probe 106 is heated to a commanded temperature very rapidly. The heating is uncontrolled, meaning that the temperature of the probe reaches the commanded temperature as rapidly as it can.

e) Scanning Mode: An area of the surface of sample 108 is selected for analysis, rather than a single point. Probe 106 is heated. The heated probe 106 is then rastered over the selected area of the surface of sample 108. Material that is ablated from sample 108 is trapped and analyzed. The temperature of probe 106 and the speed of the raster are both controllable using computer 102 and probe control process 118. The temperature of probe 106 and the speed of the raster determine the depth of the material that is ablated. For example, an area of 10 by 10 microns can be scanned with ablation occurring to 100 nanometers. This results in 10 cubic microns of ablated material. Preferably, the scanning mode is automatically controlled by computer 102. The scanning mode can also be combined with any heating mode (a)–(d) to heat probe 106.

The present invention is not limited to the above heating modes. Other modes of heating to obtain the benefits of the present invention would be known to those skilled in the art. Further, in the preferred embodiment, it is the tip of probe 106 that is heated.

In each of the heating modes, material is decomposed, desorbed or ablated for subsequent chemical analysis. Two methods of chemical analysis are used in the preferred embodiment: mass spectroscopy and gas chromatography. Both methods are well-known to those skilled in the art. There is a problem, however, associated with transferring the material to the analyzer, whether it is mass spectrometer 116 and/or gas chromatograph 115. In the preferred embodiment, this problem is solved by using a heated capillary 112. The heated capillary 112 is positioned in close proximity to probe 116, so that desorbed, decomposed or ablated species are "sucked" into capillary tube as a result of a low pressure maintained on the other side. For example, the low pressure can be generated by connecting the other end of the capillary to the vacuum chamber 134 of the mass spectrometer 116. Once the evolved material 114 has entered mass spectrometer 116, its chemical properties are analyzed in a conventional manner. In this manner, the present invention allows sub-micron study of the chemical properties of materials. Using the scanning method of heating described above, the present invention allows sub-micron chemical imaging of a sample.

The heating modes described above provide a high degree of control of the surface selectivity. The transfer mode provides information very near the surface, including the top monolayer in many cases. The temperature scanning and heat pulse modes can sample tens, and even hundreds, of microns below the surface. If an isolated particle is the object of interest, whether lying on, or buried below within a matrix with one side exposed, then the entire particle can be volatilized to ensure a good analysis with high signal to noise ratio.

As described above, the scanning mode can be combined with any of the other modes as probe 106 is rastered along the selected analysis area in two dimensions. For example, by combining the heat pulse mode and the scanning mode, probe 106 is effectively tapped on the surface of material 108 as it is rastered in two dimensions. The resulting series of gases can be analyzed by mass spectrometer 116, thus building up a chemical map of the surface of sample 108. That is, acquisition of gases is coordinated with the position in the image that is being generated.

To provide additional information a gas chromatograph 115 is added to the sub-micron chemical analysis system of the present invention. In the preferred embodiment, gas chromatograph 115 is interposed between heated capillary 112 and mass spectrometer 116, as illustrated schematically in FIG. 1. In this manner, the evolved material can be chemically analyzed by gas chromatography using gas chromatograph 115.

Using computer 102, the foregoing analyses can be automated. Preferably, areas of interest for analysis are pre-selected. This can be done by pre-selecting multiple areas on using a thermal image, such as thermal image 132. Alternately, computer 102 can select the areas of interest, for example, by using a random number generator. In addition, the heating mode is selected. This can be done by selecting the heating program. Alternately, computer 102 can select the heating mode. For example, heating control process 122, executing on computer 102, can select a default heating mode. After the selection is made, probe position process 120 causes the probe to automatically go to the first selected area. Heating mode process 122 sends appropriate probe control commands to STM 104 to cause probe 106 to heat the selected area according to the selected heating mode. The evolved gases are transferred into the analyzer through capillary 112, where their chemical nature is analyzed. After the analysis, probe position process 120 automatically causes probe 106 to move to the second pre-selected area, and the process repeats. This is done for all selected areas designated in the automatic analysis. In the automatic mode of operation different heating programs can be selected for different areas of the sample 108. For example, the first selected area can be heated according to the temperature ramp mode, while a second area can be analyzed using a scanning mode.

In some cases, it is desirable to trap the evolved gases 114 into a cryo-trap or an adsorbate (not shown). Subsequently, the material is flash desorbed and forwarded to the gas chromatograph and/or mass spectrometer for analysis.

Capillary tube 112 can be placed close to the sample by "eyeballing" the appropriate location. However, other techniques can place capillary tube 112 more accurately. In the preferred embodiment, a hunt-seek type proximity determination method is used to locate heated capillary tube 112 next to the tip of probe 106. One hunt-seek method, for example, is to use an automated micro-positioner, such as is conventionally used in optical microscopy. In this method, probe 106 and heated capillary tube 112 are made to form two halves of a capacitor. Heated capillary tube 112 is initially located by eye. Then a capacitance signal generated by the two halves is used to bring capillary tube 112 closer to probe 106, but not to close.

To prevent, capillary tube 106 from being moved too close to probe 106, a threshold for the capacitance signal can be used. If the capacitance signal exceeds the threshold, capillary tube 112 is too close to probe 106. A second threshold can be used to determine whether capillary tube 112 is close enough to probe 106. That is, if the capacitance signal is below the second threshold, then capillary tube 112 must be moved closer to probe 106. Thus, in effect a range is determined for the capacitance signal. When the capacitance signal falls within that range, capillary tube 112 is properly positioned relative to probe 106.

An alternative hunt-seek method for properly positioning capillary tube 112 relative to probe 106 is to embed a temperature sensor 136 in capillary tube 112. As before a threshold range is determined. In this case the thresholds correspond to temperatures. If the temperature sensed by temperature sensor 136 is too great, capillary tube 112 is too close to probe 106. If the temperature sensed by temperature sensor 136 is too small, capillary tube 112 is too far from probe 106.

Another alterative for properly positioning capillary tube 112 relative to probe 106 is to calibrate the micromanipulator of STM 104 and probe 106 in the x, y and z planes. By so doing, probe 106 can be precisely positioned without the need for a feedback loop based on some form of proximity determination. By calibrating the micromanipulator and probe 106 in this manner, probe 106 can be precisely positioned. As a result, capillary tube 112 can be precisely positioned relative to probe 106's known position.

Figure 2:
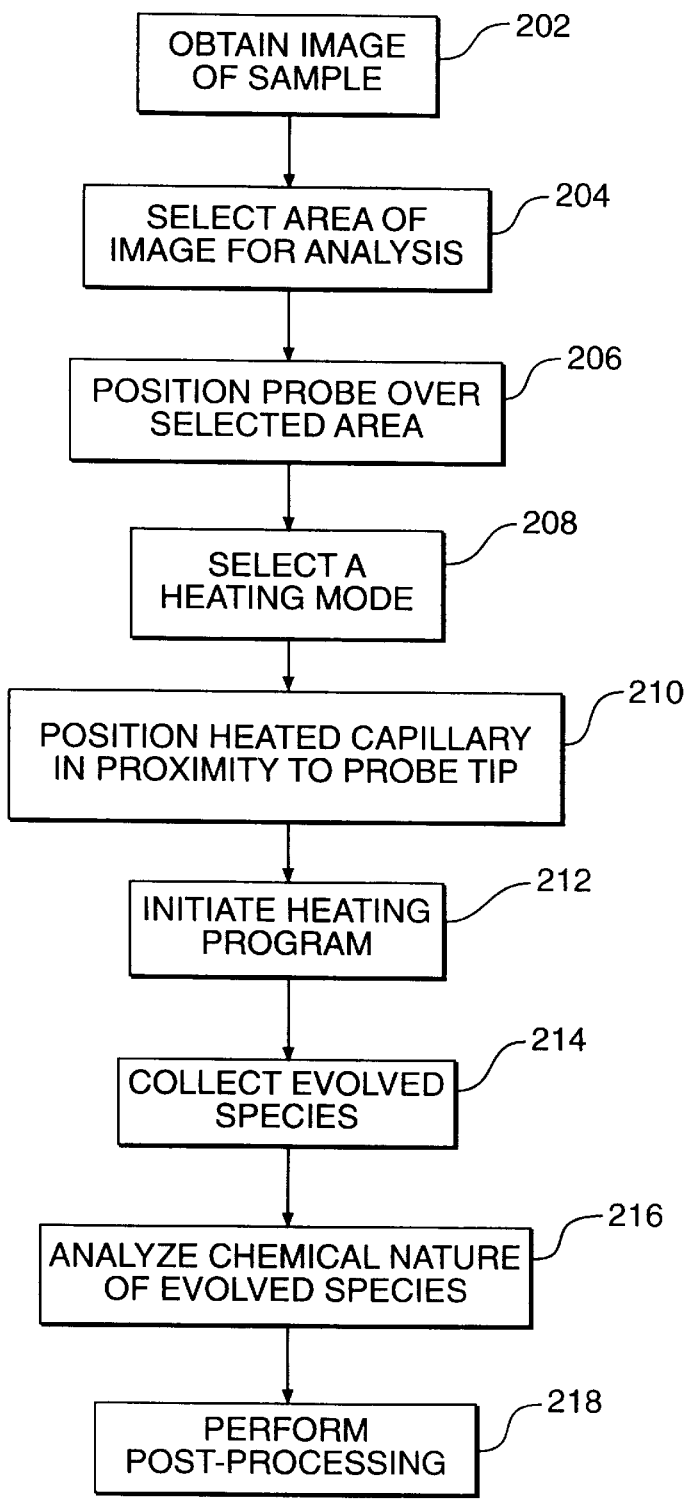
FIG. 2 is a flow chart for analyzing a sample according to a preferred embodiment of the present invention.

A preferred method for performing a process according to the present invention using the apparatus discussed above and illustrated in FIG. 1 is shown by a flow chart in FIG. 2. In step 202 an image of a sample is obtained. As described above, this image can be obtained using any imaging technique, including thermal and photothermal imaging techniques. In step 204 an area of the image is selected for analysis. This selection can be by a user or performed automatically, for example, by computer 102. In step 206, probe 106 is positioned over the selected area. In the preferred embodiment, this is done by probe position process 120, and can use the proximity determination hunt-seek or calibration methods described above. A heating mode is then selected in step 208. Once again, the selection can be by a user or automatic, for example, by computer 102 using a default. In step 210 heated capillary tube 112 is positioned in proximity to probe 106 to collect material that evolves from sample 108 upon heating. The heating mode is initiated in step 212. In the preferred embodiment, the heating mode is controlled by heating control process 122 executing on computer 102. The material that evolves is collected in step 214. The collected material is analyzed in a chemical analyzer in step 216. In the preferred embodiment, the chemical analysis is performed by gas chromatograph 115 and/or mass spectrometer 116. In step 218, any desired post-processing is performed. For example, the sample 108 from which material evolved can be analyzed to assess the volume ablated, or to image the resulting crater. Steps 202–218 can be repeated at another location if desired.

The foregoing disclosure of examples and embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A system for analyzing a sample, comprising:
    a computer;
    a scanning thermal probe microscope coupled to said computer, having:
        a sample stage having a sample disposed thereon;
        a probe to heat said sample;
    a probe control process executing on said computer to cause said probe to heat an area of said sample according to a heating mode;
    a chemical analyzer;
    a capillary tube positioned in proximity to a tip of said probe to collect gases that evolve as a result of said probe heating said sample;
    a probe position process to position said probe in proximity to said capillary tube;
    a heating control process to control heating of said probe tip;
    a first threshold for determining when said probe is too far from said capillary tube; and
    a second threshold for determining when said probe is too close to said capillary tube, wherein said first and second thresholds comprise capacitance values.

2. The system recited in claim 1, wherein the probe is cleaned by heating the probe to a high temperature.

3. A system for analyzing a sample, comprising:
    a computer;
    a scanning thermal probe microscope coupled to said computer, having:
        a sample stage having a sample disposed thereon;
        a probe to heat said sample;
    a probe control process executing on said computer to cause said probe to heat an area of said sample according to a heating mode;
    a chemical analyzer;
    a capillary tube positioned in proximity to a tip of said probe to collect gases that evolve as a result of said probe heating said sample;
    a probe position process to position said probe in proximity to said capillary tube;
    a heating control process to control heating of said probe tip;
    a first threshold for determining when said probe is too far from said capillary tube; and
    a second threshold for determining when said probe is too close to said capillary tube, wherein said first and second thresholds comprise temperature values.

4. The system recited in claim 3, wherein the probe is cleaned by heating the probe to a high temperature.

5. A method for analyzing a sample, comprising the steps of:
    (a) obtaining an image of the sample;
    (b) selecting an area of said image for analysis;
    (c) positioning a probe over said area selected in step (b);
    (d) selecting a heating mode according to which to heat the sample;
    (e) positioning a capillary tube in proximity to a tip of said probe;
    (f) initiating said heating mode;

(g) collecting material that evolves from said sample in response to said heating mode initiated in step (f); and (h) analyzing the chemical nature of said material that evolved in step (g);

wherein step (e) comprises generating a capacitance signal between the probe and the capillary tube, and using the capacitance signal to bring the capillary tube close to the probe.

6. The method recited in claim 5, further comprising the step of cleaning the probe by heating the probe to a high temperature.

7. An analytical apparatus for analyzing a sample, comprising:

(a) a scanning thermal microscope comprising a computer and a thermal probe, said scanning thermal microscope comprising means for obtaining and displaying an image of the sample;

(b) means for controlling the position of the thermal probe with respect to the sample such that a tip of the thermal probe may be placed in contact with a position on the sample corresponding to a specific point on the image of the sample;

(c) means for controlling the temperature of the tip of the thermal probe such that the temperature of a surface of the sample under the tip of the thermal probe is raised to a temperature which causes gas to evolve from the surface of the sample;

(d) a capillary tube positioned to capture the gas evolving from the surface of the sample;

(e) a chemical analytical apparatus in fluid connection with the capillary tube, for characterizing the gas evolved from the surface of the sample and captured by the capillary tube; and (f) means for precisely positioning the capillary tube relative to the thermal probe; wherein the means for precisely positioning the capillary tube relative to the thermal probe comprises means for generating a capacitance signal representative of the position of the capillary tube relative to the thermal probe.

8. The analytical apparatus recited in claim 7, further comprising means for cleaning the thermal probe by heating the probe to a high temperature.

9. An analytical apparatus for analyzing a sample, comprising:

(a) a scanning thermal microscope comprising a computer and a thermal probe, said scanning thermal microscope comprising means for obtaining and displaying an image of the sample;

(b) means for controlling the position of the thermal probe with respect to the sample such that a tip of the thermal probe may be placed in contact with a position on the sample corresponding to a specific point on the image of the sample;

(c) means for controlling the temperature of the tip of the thermal probe such that the temperature of a surface of the sample under the tip of the thermal probe is raised to a temperature which causes gas to evolve from the surface of the sample;

(d) a capillary tube positioned to capture the gas evolving from the surface of the sample;

(e) a chemical analytical apparatus in fluid connection with the capillary tube, for characterizing the gas evolved from the surface of the sample and captured by the capillary tube; and (f) means for precisely positioning the capillary tube relative to the thermal probe; wherein the means for precisely positioning the capillary tube relative to the thermal probe comprises a temperature sensor embedded in the capillary tube, and wherein the relative position of the capillary tube to the thermal probe is estimated based upon the temperature measured by the embedded temperature sensor.

10. The analytical apparatus recited in claim 9, further comprising means for cleaning the thermal probe by heating the probe to a high temperature.

11. A method for performing chemical analysis of a sample, comprising the steps of:

(a) obtaining an image of the sample using a scanning thermal microscope having a thermal probe;

(b) selecting a location on the image for chemical analysis;

(c) calculating a set of probe position control commands from the selected location;

(d) positioning the thermal probe slightly above a surface of the sample at the selected location, using the probe position control commands;

(e) selecting a heating mode and heating the thermal probe according to said selected heating mode, wherein the heating modes available for selection comprise a temperature ramp mode, a heat pulse mode and a transfer mode;

(f) driving gases off the surface of the sample;

(g) capturing gases in a capillary tube positioned next to the thermal probe; and (h) analyzing the gases in a chemical analyzer.

12. The method of claim 11, wherein the thermal probe is approximately one micron above the sample.

13. The method of claim 11, wherein the thermal probe is positioned a known distance above the surface of the sample.

14. The method of claim 11, wherein the selected heating mode is the temperature ramp mode, wherein step (e) comprises driving off adsorbed material.

15. The method of claim 14, further comprising generating gases by decomposing the surface of the sample under the thermal probe.

16. The method of claim 11, wherein the selected heating mode is the heat pulse mode.

17. The method of claim 16, wherein the thermal probe is tapped on to the surface of the sample.

18. The method of claim 16, further comprising tapping the surface of the sample according to a raster pattern.

19. The method of claim 11, wherein the chemical analyzer is a gas chromatograph.

20. The method of claim 19, wherein the gases are analyzed in a mass spectrometer after the gases have been analyzed in the gas chromatograph.

21. The method of claim 11, wherein the chemical analyzer is a mass spectrometer.

22. The method of claim 11, further comprising placing the thermal probe in contact with the surface of the sample subsequent to step (d).

23. The method of claim 22, wherein the thermal probe is kept in contact with the surface of the sample by applying a known force to the thermal probe.

24. The method of claim 11, further comprising cleaning the thermal probe by flash heating the thermal probe, and allowing the thermal probe to cool down before placing the thermal probe on the surface of the sample.

25. The method of claim 24, further comprising dipping the tip of the thermal probe into an adhesive after the thermal probe has been cleaned and before placing the thermal probe on the surface of the sample, such that when the thermal probe is placed on the sample, surface material adheres to the adhesive.

26. The method recited in claim 11, further comprising means for cleaning the thermal probe by heating the probe to a high temperature.

27. A method for performing chemical analysis of a sample, comprising the steps of:
   (a) obtaining an image of a surface of the sample using a scanning thermal microscope having a thermal probe;
   (b) selecting a location on the surface of the sample from the image for chemical analysis;
   (c) calculating a set of probe position control commands from the selected location;
   (d) positioning the thermal probe slightly above the surface of the sample at the selected location, using the set of probe position control commands;
   (e) selecting a heating mode and heating the thermal probe according to said selected heating mode;
   (f) driving gases off the surface of the sample;
   (g) capturing the gases in a capillary tube positioned next to the thermal probe;
   (h) analyzing the gases in a chemical analyzer; and
   (i) repeating steps (e)–(h) to analyze the chemical composition of the sample as a function of depth.

28. The method of claim 27, wherein the chemical analyzer is a gas chromatograph.

29. The method of claim 27, wherein the chemical analyzer is a mass spectrometer.

30. The method recited in claim 27, further comprising means for cleaning the thermal probe by heating the probe to a high temperature.

31. A method for performing chemical analysis of a sample, comprising the steps of:
   (a) obtaining an image of a surface of the sample using a scanning thermal microscope having a thermal probe;
   (b) selecting a location on the surface of the sample from the image for chemical analysis;
   (c) calculating a set of probe position control commands from the selected location;
   (d) positioning the thermal probe slightly above the surface of the sample at the selected location, using the set of probe position control commands;
   (e) selecting a heating mode and heating the thermal probe according to the selected heating mode;
   (f) driving gases off the surface of the sample;
   (g) trapping the gases in a cryo-trap;
   (h) heating the cryo-trap to release the gases from the cryo-trap; and
   (i) analyzing the gases released from the cryo-trap in a chemical analyzer.

32. The method recited in claim 31, further comprising the step of cleaning the thermal probe by heating the thermal probe to a high temperature.

33. A method for performing chemical analysis of a sample, comprising the steps of:
   (a) obtaining an image of a surface of the sample using a scanning thermal microscope having a thermal probe;
   (b) selecting a location on the surface of the sample using a scanning thermal microscope having a thermal probe;
   (c) calculating a set of probe position commands from the selected location;
   (d) positioning the thermal probe slightly above the surface of the sample at the selected location, using a set of probe position control commands;
   (e) selecting a heating mode and heating the thermal probe according to said selected heating mode;
   (f) driving gases off the surface of the sample;
   (g) trapping the gases in an adsorbate;
   (h) flash heating the adsorbate to desorb the gases; and
   (i) analyzing the desorbed gases in a chemical analyzer.

34. The method recited in claim 33, further comprising the step of cleaning the thermal probe by heating the thermal probe to a high temperature.

35. An analytical apparatus, comprising:
   (a) a computer and a probe for obtaining and displaying an image of a sample;
   (b) means for controlling the position of the probe with respect to the sample such that a tip of the probe is placed in contact with a position on a surface of the sample corresponding to a specific point on the image of the sample;
   (c) means for controlling the temperature of the tip of the probe such that the temperature of the surface of the sample with which the tip of the probe is in contact is raised to a temperature which causes gas to evolve from the surface of the sample;
   (d) a capillary tube positioned to capture the gas evolving from the surface of the sample;
   (e) a chemical analytical apparatus in fluid connection with the capillary tube, for characterizing the gas evolved from the surface of the sample captured by the capillary tube; and
   (f) means for precisely positioning the capillary tube relative to the probe, wherein the means for precisely positioning the capillary tube relative to the probe comprises means for generating a capacitance signal representative of the position of the capillary tube relative to the probe.

36. The analytical apparatus recited in claim 35, further comprising means for cleaning the probe by heating the probe to a high temperature.

37. An analytical apparatus, comprising:
   (a) a computer and a probe for obtaining and displaying an image of a sample;
   (b) means for controlling the position of the probe with respect to the sample such that a tip of the probe is placed in contact with a position on a surface of the sample corresponding to a specific point on the image of the sample;
   (c) means for controlling the temperature of the tip of the probe such that the temperature of the surface of the sample with which the tip of the probe is in contact is raised to a temperature which causes gas to evolve from the surface of the sample;
   (d) a capillary tube positioned to capture the gas evolving from the surface of the sample;
   (e) a chemical analytical apparatus in fluid connection with the capillary tube, for characterizing the gas evolved from the surface of the sample captured by the capillary tube; and
   (f) means for precisely positioning the capillary tube relative to the probe, wherein the means for precisely positioning the capillary tube relative to the probe comprises a temperature sensor embedded in the capillary tube, and wherein the relative position of the capillary tube to the probe is estimated based upon the temperature measured by the embedded temperature sensor.

38. The analytical apparatus recited in claim 37, further comprising means for cleaning the probe by heating the probe to a high temperature.

* * * * *